(12) United States Patent
Ortiz et al.

(10) Patent No.: US 8,876,844 B2
(45) Date of Patent: Nov. 4, 2014

(54) ANASTOMOSIS REINFORCEMENT USING BIOSURGICAL ADHESIVE AND DEVICE

(75) Inventors: Mark S. Ortiz, Milford, OH (US); Fredrick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 2021 days.

(21) Appl. No.: 11/555,392

(22) Filed: Nov. 1, 2006

(65) Prior Publication Data

US 2008/0147101 A1  Jun. 19, 2008

(51) Int. Cl.
*A61B 17/08* (2006.01)
*A61B 17/11* (2006.01)
A61B 17/3205 (2006.01)
A61B 17/29 (2006.01)
A61B 17/10 (2006.01)

(52) U.S. Cl.
CPC .......... *A61B 17/1114* (2013.01); *A61B 17/083* (2013.01); *A61B 17/32053* (2013.01); *A61B 17/29* (2013.01); *A61B 17/10* (2013.01); *A61B 2017/1139* (2013.01)
USPC ............ 606/153; 606/151; 606/155; 606/214

(58) Field of Classification Search
USPC ......... 606/151, 153, 139, 142, 155, 157, 158, 606/213–215
See application file for complete search history.

(56) References Cited

U.S. PATENT DOCUMENTS

| | | | |
|---|---|---|---|
| 4,735,616 A | 4/1988 | Eibl et al. | |
| 4,766,898 A | 8/1988 | Hardy et al. | |
| 4,874,368 A | 10/1989 | Miller et al. | |
| 5,004,469 A | 4/1991 | Palmieri et al. | |
| 5,154,320 A | 10/1992 | Bolduc | |
| 5,254,113 A | 10/1993 | Wilk | |
| 5,312,333 A | 5/1994 | Churinetz et al. | |

(Continued)

FOREIGN PATENT DOCUMENTS

| | | |
|---|---|---|
| EP | 0315222 B1 | 11/1992 |
| EP | 0716833 A2 | 6/1996 |

(Continued)

OTHER PUBLICATIONS

Ikeda, et al.; "Auxiliary Tool for Device for Applying Adhesive on Living Tissue;" published in Japan [translated abstract for Patent Application No. JP2000286958]; Jun. 12, 2001.

(Continued)

*Primary Examiner* — Dianne Dornbusch
*Assistant Examiner* — Alexander Orkin
(74) *Attorney, Agent, or Firm* — Frost Brown Todd LLC (57) ABSTRACT

An exemplary anastomosis device comprises a proximal ring, a distal ring, and a middle ring. The middle ring has apertures configured to communicate a fluid such as an adhesive. The exemplary anastomosis device also has arms joining the proximal ring to the center member and arms joining the distal ring to the center member. The anastomosis device is configured to move from an unactuated position, where it has a generally cylindraceous configuration, to an actuated position, where it has a generally rivet-like configuration. The anastomosis device may be used to provide and secure an anastomosis between adjacent tissue walls. Adhesive may be communicated through the apertures of the middle ring of the anastomosis device to seal or strengthen the anastomosis. An applier may be used to deploy the anastomosis device and to communicate the adhesive through the apertures.

19 Claims, 11 Drawing Sheets

(56) References Cited

U.S. PATENT DOCUMENTS

| | | | |
|---|---|---|---|
| 5,324,305 A | 6/1994 | Kanner | |
| 5,372,585 A | 12/1994 | Tiefenbrun et al. | |
| 5,443,481 A | 8/1995 | Lee | |
| 5,474,540 A | 12/1995 | Miller et al. | |
| 5,529,577 A | 6/1996 | Hammerslag | |
| 5,582,596 A | 12/1996 | Fukunaga et al. | |
| 5,605,541 A | 2/1997 | Holm | |
| 5,718,711 A | 2/1998 | Berenstein et al. | |
| 5,752,965 A | 5/1998 | Francis et al. | |
| 5,759,169 A | 6/1998 | Marx | |
| 5,759,171 A | 6/1998 | Coelho et al. | |
| 5,814,022 A | 9/1998 | Antanavich et al. | |
| 5,844,087 A | 12/1998 | Zimmerman et al. | |
| 5,853,422 A * | 12/1998 | Huebsch et al. | 606/213 |
| 5,895,412 A | 4/1999 | Tucker | |
| 5,928,611 A | 7/1999 | Leung | |
| 5,981,621 A | 11/1999 | Clark et al. | |
| 6,007,515 A | 12/1999 | Epstein et al. | |
| 6,010,714 A | 1/2000 | Leung et al. | |
| 6,055,828 A | 5/2000 | Rivera et al. | |
| 6,099,807 A | 8/2000 | Leung | |
| 6,113,571 A | 9/2000 | Zinger et al. | |
| 6,143,352 A | 11/2000 | Clark et al. | |
| 6,143,805 A | 11/2000 | Hickey et al. | |
| 6,162,239 A | 12/2000 | Manhes | |
| 6,174,919 B1 | 1/2001 | Hickey | |
| 6,183,593 B1 | 2/2001 | Narang et al. | |
| 6,206,905 B1 | 3/2001 | Holm et al. | |
| 6,217,603 B1 | 4/2001 | Clark et al. | |
| 6,228,051 B1 | 5/2001 | Trumbull | |
| 6,234,994 B1 | 5/2001 | Zinger | |
| 6,245,933 B1 | 6/2001 | Malofsky et al. | |
| 6,280,399 B1 | 8/2001 | Rossin et al. | |
| 6,283,933 B1 | 9/2001 | D'Alessio et al. | |
| 6,302,898 B1 | 10/2001 | Edwards et al. | |
| 6,306,243 B1 | 10/2001 | Clark et al. | |
| 6,310,166 B1 | 10/2001 | Hickey et al. | |
| 6,322,852 B1 | 11/2001 | Leung | |
| 6,325,810 B1 | 12/2001 | Hamilton et al. | |
| 6,340,097 B1 | 1/2002 | D'Alessio et al. | |
| 6,352,704 B1 | 3/2002 | Nicholson et al. | |
| 6,372,313 B1 | 4/2002 | D'Alessio et al. | |
| 6,376,019 B1 | 4/2002 | Leung | |
| 6,394,975 B1 | 5/2002 | Epstein | |
| 6,394,982 B1 | 5/2002 | Ehrenfels | |
| 6,398,797 B2 | 6/2002 | Bombard et al. | |
| 6,412,639 B1 | 7/2002 | Hickey | |
| 6,420,590 B1 | 7/2002 | Badejo et al. | |
| 6,425,704 B2 | 7/2002 | Voiers et al. | |
| 6,428,233 B1 | 8/2002 | Clark et al. | |
| 6,428,234 B1 | 8/2002 | Bobo et al. | |
| 6,432,084 B1 | 8/2002 | Levinson et al. | |
| 6,433,096 B1 | 8/2002 | Hickey et al. | |
| 6,439,789 B1 | 8/2002 | Balance et al. | |
| 6,454,739 B1 | 9/2002 | Chang | |
| 6,455,064 B1 | 9/2002 | Narang et al. | |
| 6,458,095 B1 | 10/2002 | Wirt et al. | |
| 6,461,361 B1 | 10/2002 | Epstein | |
| 6,461,367 B1 | 10/2002 | Kirsch et al. | |
| 6,464,663 B1 | 10/2002 | Zinger | |
| 6,468,520 B1 | 10/2002 | Rowe et al. | |
| 6,471,670 B1 | 10/2002 | Enrenfels et al. | |
| 6,478,191 B1 | 11/2002 | D'Alessio et al. | |
| 6,488,197 B1 | 12/2002 | Whitman | |
| 6,488,650 B1 | 12/2002 | Epstein et al. | |
| 6,488,944 B2 | 12/2002 | Narang | |
| 6,491,201 B1 | 12/2002 | Whitman | |
| 6,494,896 B1 | 12/2002 | D'Alessio et al. | |
| 6,512,023 B1 | 1/2003 | Malofsky et al. | |
| 6,527,749 B1 | 3/2003 | Roby et al. | |
| 6,540,716 B1 | 4/2003 | Holm | |
| 6,547,467 B2 | 4/2003 | Quintero | |
| 6,565,840 B1 | 5/2003 | Clark et al. | |
| 6,579,469 B1 | 6/2003 | Nicholson et al. | |
| 6,585,967 B2 | 7/2003 | Narang et al. | |
| 6,589,269 B2 | 7/2003 | Zhu et al. | |
| 6,592,281 B2 | 7/2003 | Clark et al. | |
| 6,595,940 B1 | 7/2003 | D'Alessio et al. | |
| 6,602,496 B2 | 8/2003 | Hedgpeth et al. | |
| 6,605,667 B1 | 8/2003 | Badejo et al. | |
| 6,607,631 B1 | 8/2003 | Badejo et al. | |
| 6,613,020 B1 | 9/2003 | Holm et al. | |
| 6,616,019 B2 | 9/2003 | D'Alessio et al. | |
| 6,620,846 B1 | 9/2003 | Jonn et al. | |
| 6,637,967 B2 | 10/2003 | Bobo et al. | |
| 6,666,873 B1 | 12/2003 | Cassell | |
| 6,676,322 B1 | 1/2004 | Leung | |
| 6,681,979 B2 | 1/2004 | Whitman | |
| 6,695,199 B2 | 2/2004 | Whitman | |
| 6,705,790 B2 | 3/2004 | Quintero et al. | |
| 6,719,768 B1 * | 4/2004 | Cole et al. | 606/153 |
| 6,743,858 B2 | 6/2004 | Hickey et al. | |
| 6,746,667 B2 | 6/2004 | Badejo et al. | |
| 6,748,950 B2 | 6/2004 | Clark et al. | |
| 6,764,467 B1 | 7/2004 | Roby et al. | |
| 6,767,552 B2 | 7/2004 | Narang | |
| 6,779,657 B2 | 8/2004 | Mainwaring et al. | |
| 6,783,514 B2 | 8/2004 | Tovey et al. | |
| 6,802,416 B1 | 10/2004 | D'Alessio et al. | |
| 6,802,822 B1 | 10/2004 | Dodge | |
| 6,811,341 B2 | 11/2004 | Crane | |
| D500,085 S | 12/2004 | Cotter et al. | |
| 6,837,027 B2 | 1/2005 | Hickey | |
| 6,863,660 B2 | 3/2005 | Marx | |
| 6,884,232 B1 | 4/2005 | Hagmann et al. | |
| 6,896,684 B2 | 5/2005 | Monassevitch et al. | |
| 6,896,838 B2 | 5/2005 | D'Alessio | |
| 6,921,381 B2 | 7/2005 | Spero et al. | |
| 6,942,875 B2 | 9/2005 | Hedgpeth | |
| 6,960,040 B2 | 11/2005 | D'Alessio et al. | |
| 7,037,344 B2 | 5/2006 | Kagan et al. | |
| 7,608,086 B2 | 10/2009 | Tanaka et al. | |
| 2002/0012678 A1 | 1/2002 | Narang | |
| 2002/0037310 A1 | 3/2002 | Jonn et al. | |
| 2002/0048480 A1 | 4/2002 | D'Alessio et al. | |
| 2002/0055573 A1 | 5/2002 | Malofsky et al. | |
| 2002/0065336 A1 | 5/2002 | Hickey et al. | |
| 2002/0119184 A1 | 8/2002 | Nicholson et al. | |
| 2002/0147462 A1 | 10/2002 | Mair et al. | |
| 2002/0156203 A1 | 10/2002 | Hickey et al. | |
| 2002/0157675 A1 | 10/2002 | Clark et al. | |
| 2002/0165483 A1 | 11/2002 | Miller et al. | |
| 2002/0173770 A1 | 11/2002 | Flory et al. | |
| 2002/0176732 A1 | 11/2002 | Quintero et al. | |
| 2002/0176733 A1 | 11/2002 | Clark et al. | |
| 2002/0185396 A1 | 12/2002 | Mainwaring et al. | |
| 2002/0192011 A1 | 12/2002 | Bobo et al. | |
| 2002/0192107 A1 | 12/2002 | Hickey | |
| 2003/0007826 A1 | 1/2003 | Badejo et al. | |
| 2003/0007946 A1 | 1/2003 | Narang et al. | |
| 2003/0007947 A1 | 1/2003 | Narang | |
| 2003/0007948 A1 | 1/2003 | Hedgpeth | |
| 2003/0007949 A1 | 1/2003 | Hedgpeth et al. | |
| 2003/0015557 A1 | 1/2003 | D'Alessio et al. | |
| 2003/0031499 A1 | 2/2003 | Heard et al. | |
| 2003/0032833 A1 | 2/2003 | Badejo et al. | |
| 2003/0032967 A1 | 2/2003 | Park et al. | |
| 2003/0039781 A1 | 2/2003 | D'Alessio et al. | |
| 2003/0044219 A1 | 3/2003 | Quintero | |
| 2003/0060380 A1 | 3/2003 | Ayarza et al. | |
| 2003/0063944 A1 | 4/2003 | Leung | |
| 2003/0080151 A1 | 5/2003 | D'Alessio et al. | |
| 2003/0082116 A1 | 5/2003 | Badejo et al. | |
| 2003/0096069 A1 | 5/2003 | D'Alessio | |
| 2003/0149128 A1 | 8/2003 | Malofsky et al. | |
| 2003/0181964 A1 | 9/2003 | Sharkey et al. | |
| 2003/0202956 A1 | 10/2003 | Clark et al. | |
| 2004/0026282 A1 | 2/2004 | D'Alessio et al. | |
| 2004/0059283 A1 | 3/2004 | Kirwan et al. | |
| 2004/0111115 A1 | 6/2004 | Maw | |
| 2004/0120849 A1 | 6/2004 | Stewart et al. | |
| 2004/0137067 A1 | 7/2004 | Narang et al. | |
| 2004/0143290 A1 | 7/2004 | Brightbill | |
| 2004/0151688 A1 | 8/2004 | Sherbondy et al. | |

(56) References Cited

U.S. PATENT DOCUMENTS

| | | |
|---|---|---|
| 2004/0190975 A1 | 9/2004 | Goodman et al. |
| 2004/0223932 A1 | 11/2004 | Hedgpeth et al. |
| 2004/0223946 A1 | 11/2004 | Kidd et al. |
| 2004/0234578 A1 | 11/2004 | Chen et al. |
| 2004/0243155 A1* | 12/2004 | Yencho et al. ............... 606/153 |
| 2004/0254561 A1 | 12/2004 | Stenton |
| 2005/0033328 A1 | 2/2005 | Laufer et al. |
| 2005/0042266 A1 | 2/2005 | Narang |
| 2005/0047846 A1 | 3/2005 | Narang et al. |
| 2005/0070935 A1 | 3/2005 | Ortiz |
| 2005/0070939 A1* | 3/2005 | Beaupre ..................... 606/154 |
| 2005/0145671 A1 | 7/2005 | Viola |
| 2005/0147457 A1 | 7/2005 | Badejo et al. |
| 2005/0175395 A1 | 8/2005 | Quintero et al. |
| 2005/0182443 A1 | 8/2005 | Jonn et al. |
| 2005/0184121 A1 | 8/2005 | Heinrich |
| 2005/0220849 A1 | 10/2005 | Hickey |
| 2005/0228446 A1 | 10/2005 | Mooradian et al. |
| 2005/0230453 A1 | 10/2005 | Viola |
| 2005/0256446 A1 | 11/2005 | Criscuolo et al. |
| 2006/0009099 A1 | 1/2006 | Jonn et al. |
| 2006/0135992 A1* | 6/2006 | Bettuchi et al. ............. 606/219 |
| 2007/0142850 A1* | 6/2007 | Fowler ........................ 606/153 |

FOREIGN PATENT DOCUMENTS

| | | |
|---|---|---|
| EP | 0648510 B1 | 11/1998 |
| EP | 0669100 B1 | 11/1998 |
| EP | 1078600 A2 | 2/2001 |
| EP | 1159081 A1 | 12/2001 |
| EP | 1381321 A2 | 1/2004 |
| EP | 1113839 B1 | 11/2004 |
| EP | 1073484 B1 | 8/2005 |
| EP | 1411836 B1 | 10/2005 |
| JP | 10262986 | 10/1998 |
| JP | 2000217830 | 8/2000 |
| JP | 2001157716 | 6/2001 |
| JP | 2001190558 | 7/2001 |
| JP | 2002233581 | 8/2002 |
| JP | 2003126268 | 5/2003 |
| JP | 2005028009 | 2/2005 |
| JP | 2005169125 | 6/2005 |
| WO | WO 92/09651 | 6/1992 |
| WO | WO 95/31137 A1 | 11/1995 |
| WO | WO 98/41154 A1 | 9/1998 |
| WO | WO 99/17833 A1 | 4/1999 |
| WO | WO 99/30629 A1 | 6/1999 |
| WO | WO 01/12257 A1 | 2/2001 |
| WO | WO 01/24869 A1 | 4/2001 |
| WO | WO 01/62158 A2 | 8/2001 |
| WO | WO 01/62162 A1 | 8/2001 |
| WO | WO 01/62333 A1 | 8/2001 |
| WO | WO 02/067785 A2 | 9/2002 |
| WO | WO 03/088845 | 10/2003 |

OTHER PUBLICATIONS

Ikeda, et al.; "Device for Applying Organism Tissue Adhesive;" published in Japan [translated abstract for Patent Application No. JP2000320375]; Jul. 17, 2001.

Gomibuchi, Makoto; "Medical Adhesive Applicator;" published in Japan [translated abstract for Patent Application No. JP11023146]; Aug. 8, 2000.

Ikeda, et al.; "Organism-Tissue Adhesive Applicator;" published in Japan [translated abstract for Patent Application No. JP2001033756]; Aug. 20, 2002.

Ikeda, et al.; "Biological Tissue Adhesive Applicator;" published in Japan [translated abstract for Patent Application No. JP2001323890]; May 7, 2003.

Arikawa, Seiki; "Biological Tissue Adhesive Applicator;" published in Japan [translated abstract for Patent Application No. JP2003273091]; Feb. 3, 2005.

Keller, Wilhelm A.; "Applicator for Dispensing Appliance;" published in Japan [translated abstract for Patent Application No. JP2004358509]; Jun. 30, 2005.

Sasaki, Hiroshi; "Adhesive Agent Applicator for Surgical Operation;" published in Japan [translated abstract for Patent Application No. JP09076817]; Oct. 6, 1998.

* cited by examiner

ANASTOMOSIS REINFORCEMENT USING BIOSURGICAL ADHESIVE AND DEVICE

BACKGROUND

Morbid obesity creates significant medical issues, often warranting treatment. One method of treating morbid obesity includes the use of anastomotic devices to create an anastomosis between two gastrointestinal tissue walls. Examples of such anastomosis devices are disclosed in U.S. Pub. No. 2005/0070935, the disclosure of which is incorporated by reference herein. While a variety of systems and methods have been made and used for creating anastomoses between gastrointestinal tissue walls or other body lumens, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
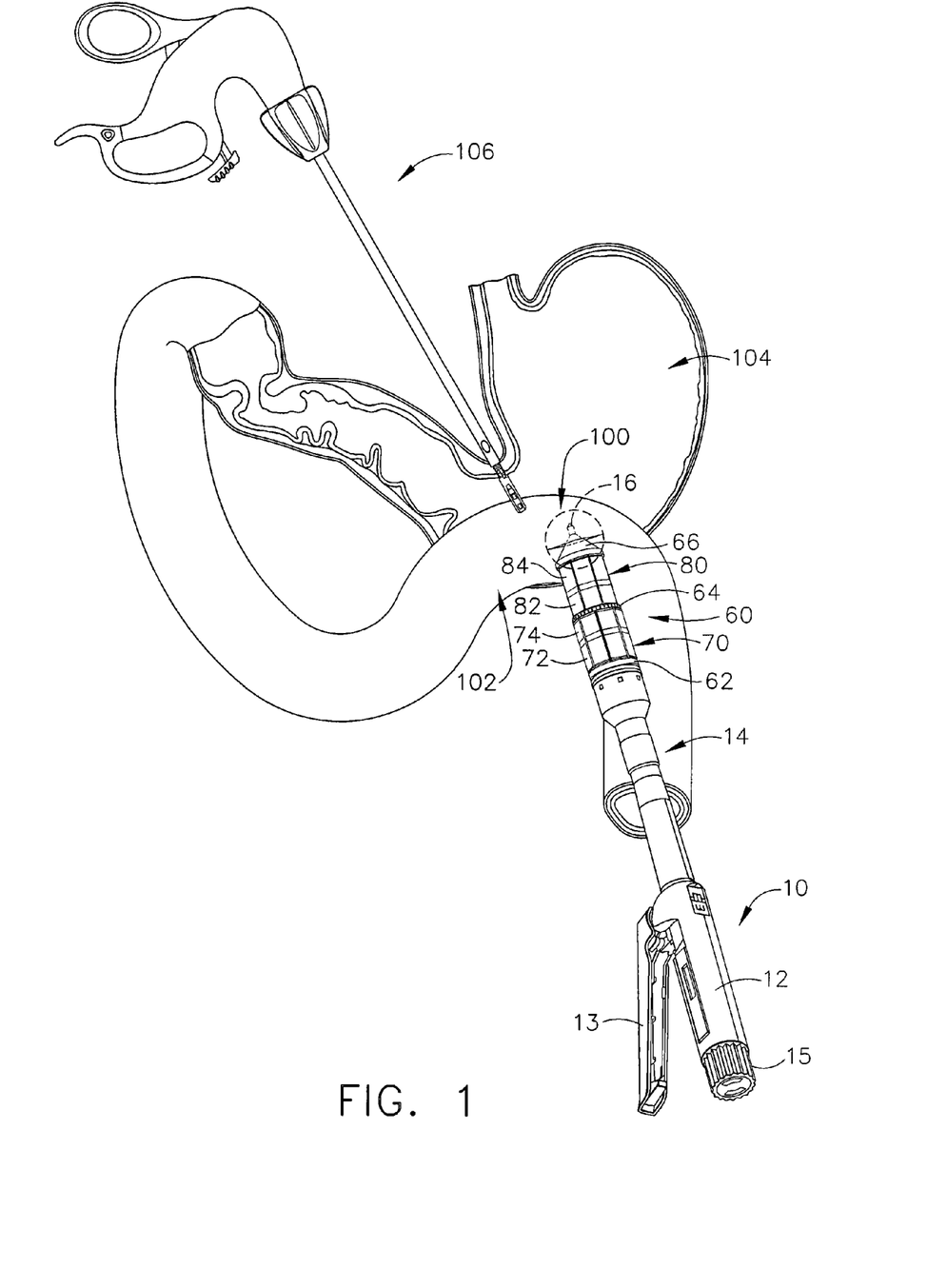
FIG. 1 depicts a partial cross-sectional perspective view of an exemplary anastomotic device being applied to an anastomosis site.

FIG. 1 depicts an exemplary anastomosis site (100) in the context of a gastric bypass procedure. As shown, a patient's jejunum (102) is grasped by a set of graspers (106) and is positioned such that an anastomosis may be formed between the jejunum (102) and the patient's stomach (104). The graspers (106) shown are conventional graspers (106), and are being shown for merely illustrative purposes only. It will be appreciated that any other type of graspers (106) or any other device(s) may be used to position the jejunum (102) for an anastomosis. In the present example, the anastomosis that is to be created at the anastomosis site (100) is configured to provide a gastric bypass as a treatment for morbid obesity. It will be appreciated, however, that anastomoses may be created in a variety of other places in a patient for a variety of other purposes. Furthermore, gastric bypasses may be provided for purposes other than treatment of morbid obesity.

One technique for providing an anastomosis is to use an anastomotic ring device. An exemplary anastomotic ring device is disclosed in U.S. Pub. No. 2005/0070935 to Ortiz, the disclosure of which is incorporated by reference herein. Another exemplary anastomotic ring device is disclosed in U.S. Pub. No. 2003/0032967 to Park et al., the disclosure of which is incorporated by reference herein. Yet another exemplary anastomotic ring device is disclosed in U.S. Pub. No. 2005/0070934 to Tanaka et al., the disclosure of which is incorporated by reference herein. Other suitable anastomotic ring devices will be apparent to those of ordinary skill in the art, while another exemplary anastomotic ring device (60) will be described in greater detail below. In particular, the anastomotic ring device (60) of the present example is shown in FIG. 1, positioned on an exemplary applier device (10), which will also be described in greater detail below.

Figure 2:
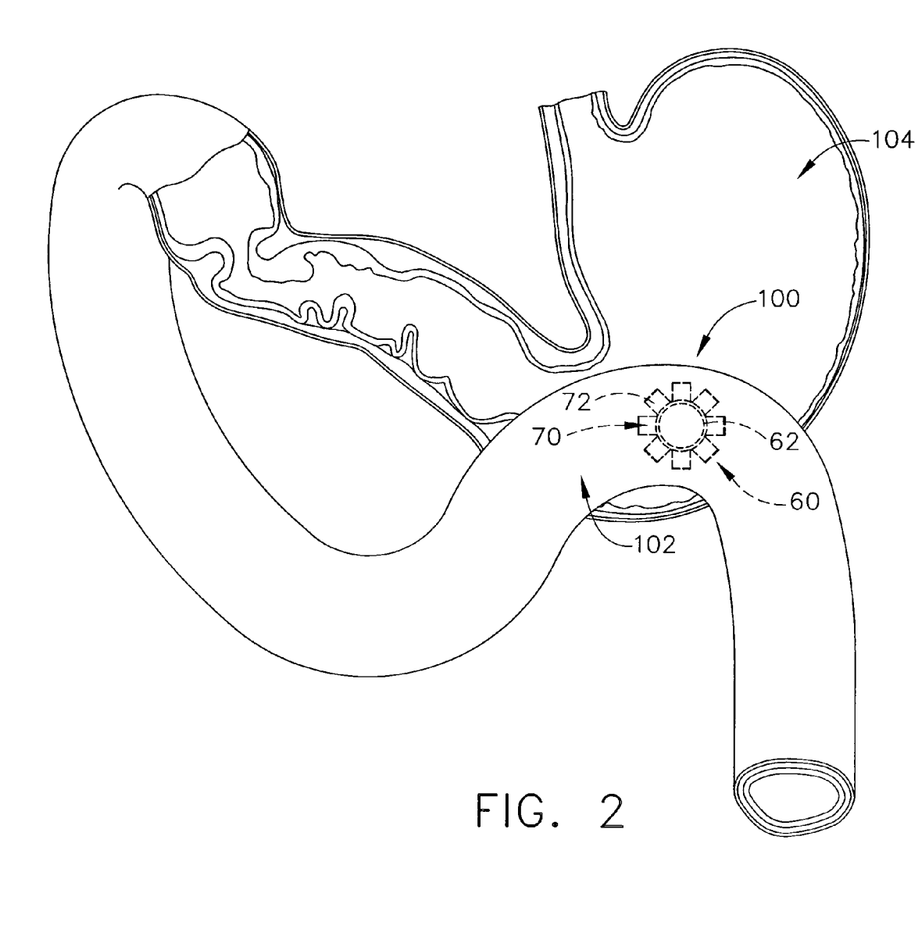
FIG. 2 depicts a partial cross-sectional perspective view of the anastomotic device of FIG. 1 deployed at an anastomosis side.
Figure 3:
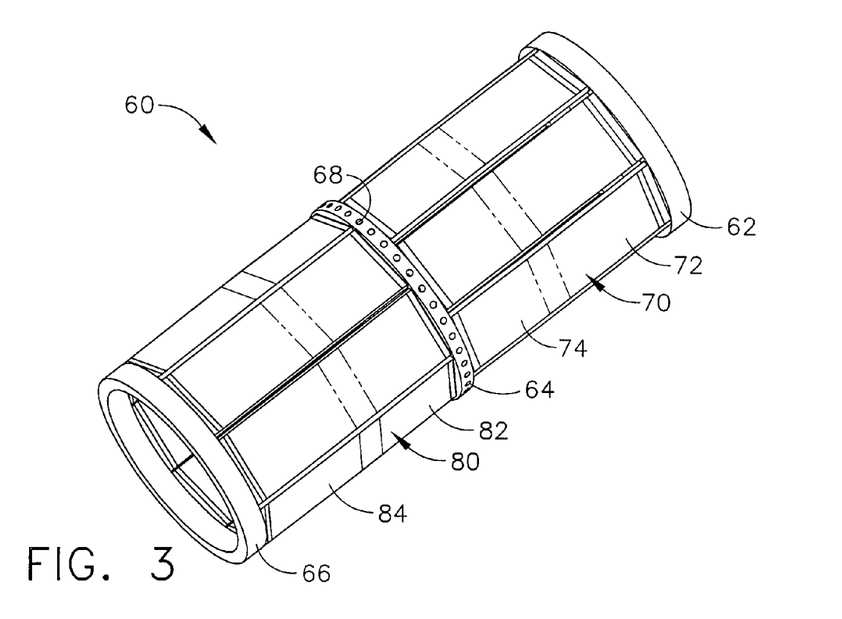
FIG. 3 depicts a perspective view of the anastomotic device of FIG. 1 in an exemplary pre-deployed configuration.
Figure 4:
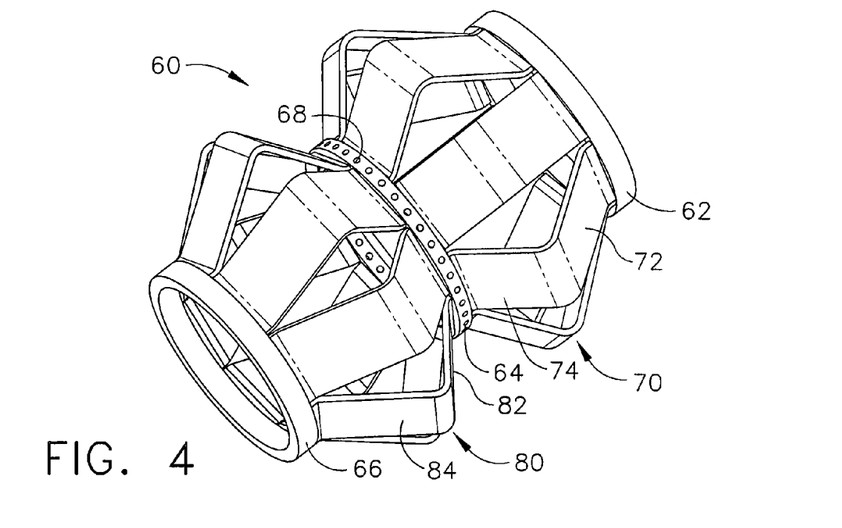
FIG. 4 depicts a perspective view of the anastomotic device of FIG. 1 in an exemplary partially deployed configuration.
Figure 5:
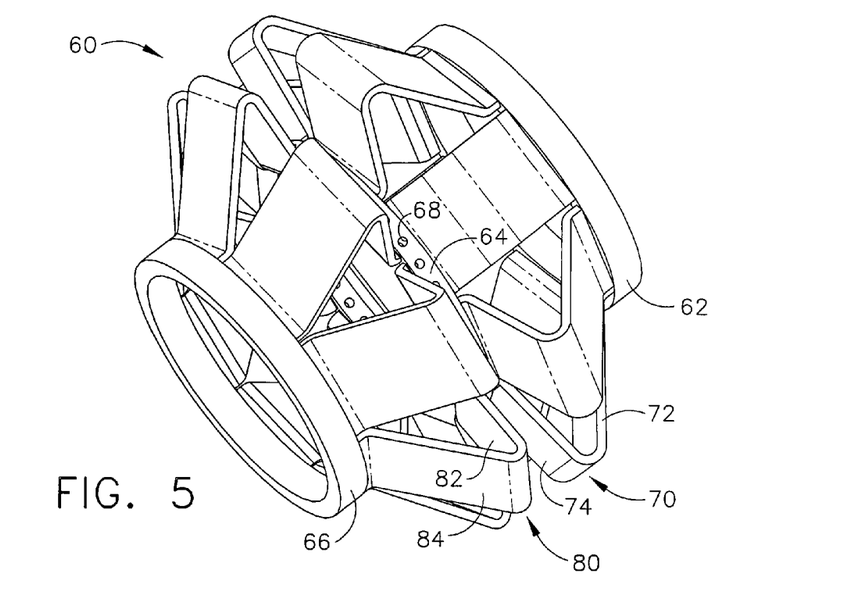
FIG. 5 depicts a perspective view of the anastomotic device of FIG. 1 in an exemplary deployed configuration.
Figure 6:
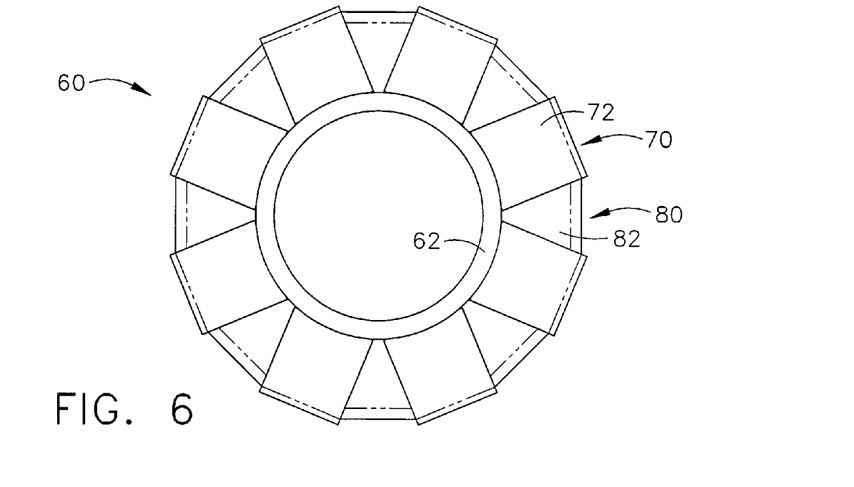
FIG. 6 depicts a plan view of the anastomotic device of FIG. 5.
Figure 7:
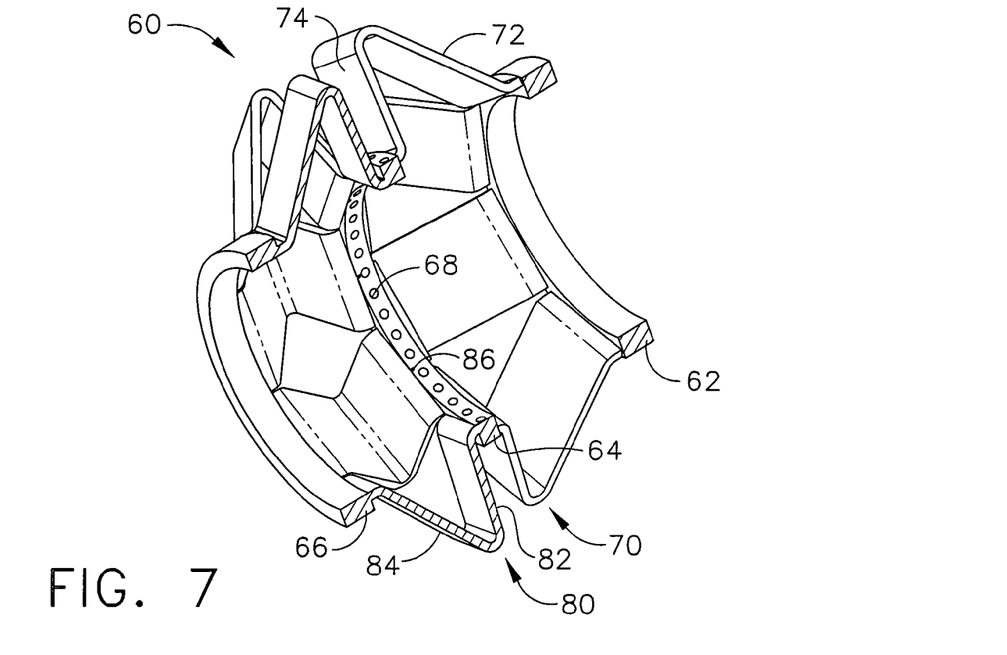
FIG. 7 depicts a perspective cross-sectional view of the anastomotic device of FIG. 5.
Figure 8:
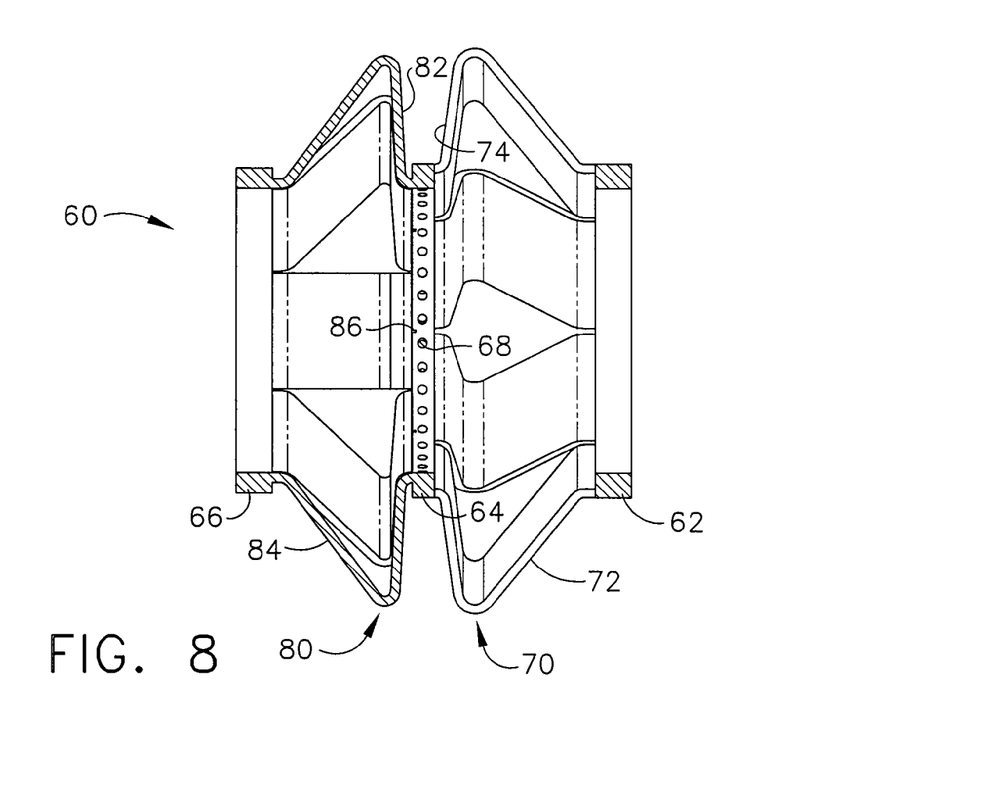
FIG. 8 depicts a cross-sectional view of the anastomotic device of FIG. 5.
Figure 9:
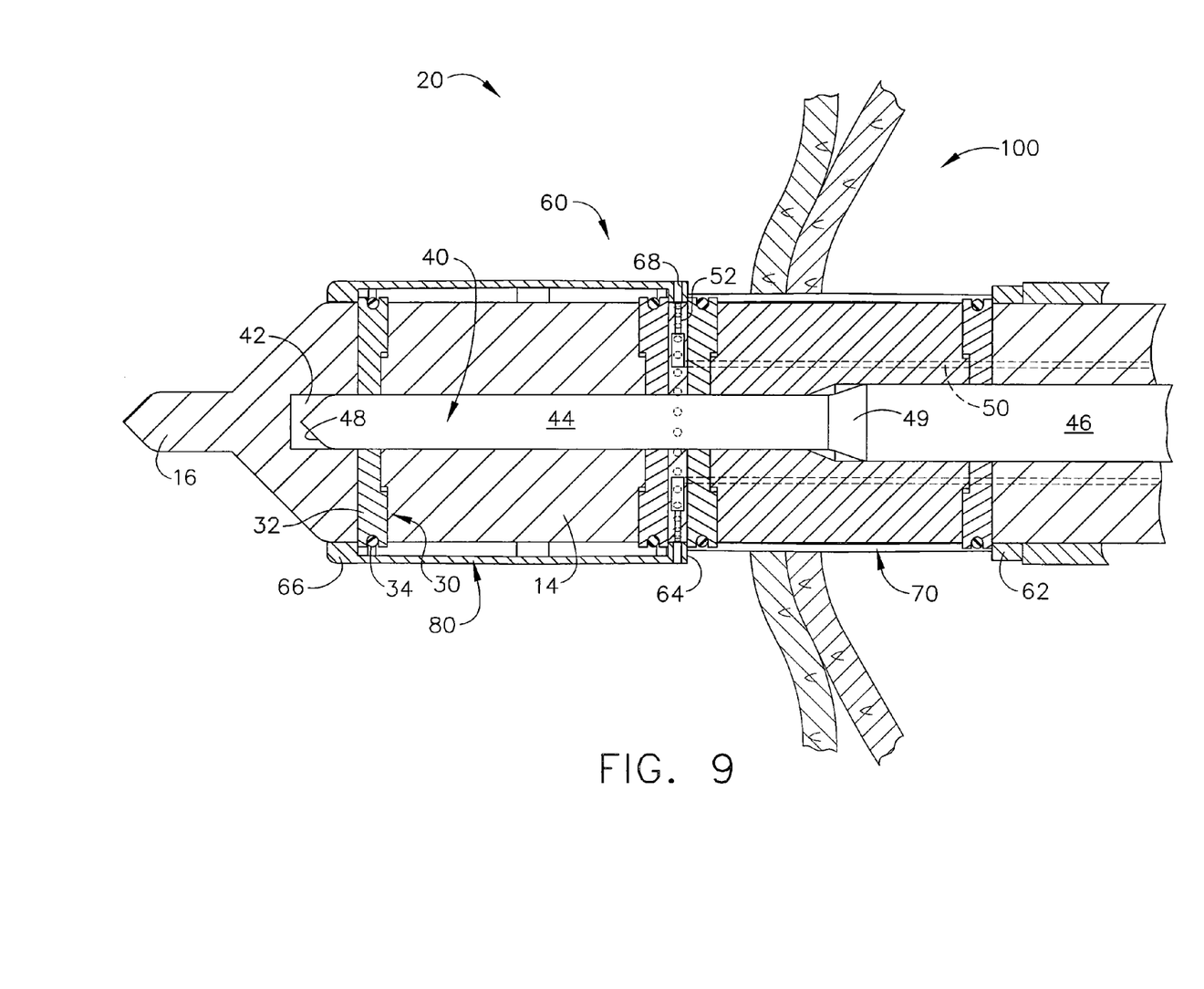
FIG. 9 depicts a partial cross-sectional view of the anastomosis device of FIG. 1 on an exemplary applier, with the anastomosis device in an exemplary pre-deployed configuration.
Figure 10:
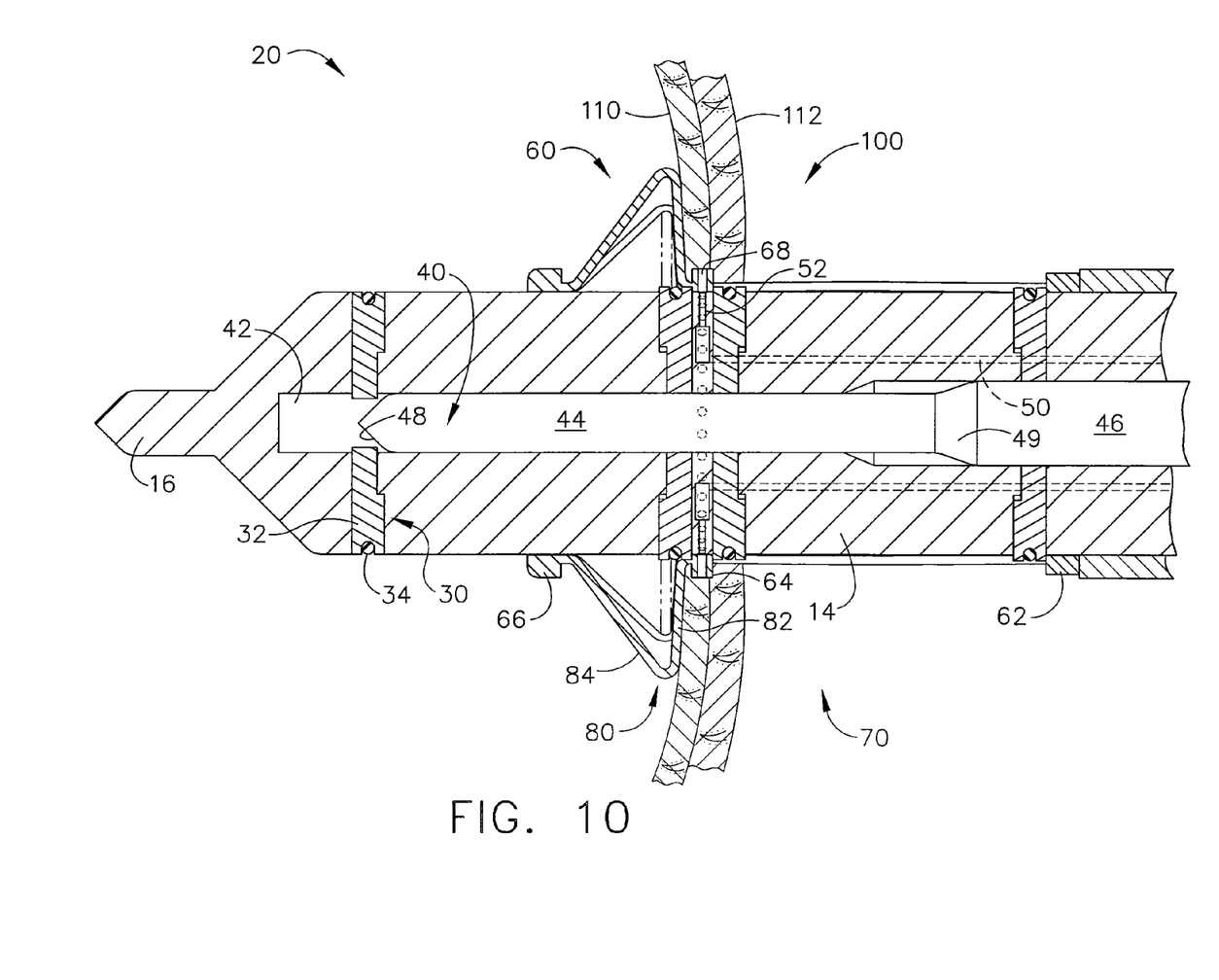
FIG. 10 depicts a partial cross-sectional view of the anastomosis device and applier of FIG. 9, with a distal portion of the anastomosis device in a deployed configuration.

As shown in FIGS. 1-14, the anastomotic ring device (60) of the present example is operable to move from an unactuated position to an actuated position. For instance, as shown in FIGS. 1, 3, and 9, anastomotic ring device (60) in an unactuated position has a generally cylindraceous configuration. As shown in FIGS. 2, 5-8, and 11-13, anastomotic ring device (60) in an actuated position has a rivet-like configuration. Various exemplary partially-actuated positions are illustrated in FIGS. 4 and 10. As will be described in greater detail below, anastomotic ring device (60) of the present example is configured to be inserted through an opening formed in two lumens (e.g., an opening in stomach (104) and an opening in jejunum (102)) when in an unactuated position, and is then configured to provide and secure an anastomosis between the two lumens when in an actuated position.

Anastomotic ring device (60) comprises a proximal ring (62), a middle ring (64), and a distal ring (66). Rings (62, 64, 66) lie along a common axis. Proximal ring (62) is attached to middle ring (64) via a plurality of proximal arms (70). Each proximal arm (70) comprises a first segment (72) and a second segment (74). Each first segment (72) of each proximal arm (70) is in a hinged relationship with the second segment (72) of the corresponding proximal arm (70). Each first segment (72) of each proximal arm (70) is also in a hinged relationship with proximal ring (62). Each second segment (74) of each proximal arm (70) is in a hinged relationship with middle ring (64). In other words, proximal arms (70) are configured to hingedly flex, such that proximal ring (62) may be moved in a longitudinal direction toward and away from middle ring (64). In the present example, proximal arms (70) comprise a unitary plastic material, such that the hinged relationships described above are provided by bending of the material. Alternatively, proximal arms (70) may comprise other materials or configurations (e.g., first segment (72) and second segment (74) may be separate pieces joined together).

Similarly, distal ring (66) is attached to middle ring (64) via a plurality of distal arms (80). Each distal arm (80) comprises a first segment (82) and a second segment (84). Each first segment (82) of each distal arm (80) is in a hinged relationship with the second segment (82) of the corresponding distal arm (80). Each first segment (82) of each distal arm (80) is also in a hinged relationship with distal ring (66). Each second segment (84) of each distal arm (80) is in a hinged relationship with middle ring (64). In other words, distal arms (80) are configured to hingedly flex, such that distal ring (82) may be moved in a longitudinal direction toward and away from middle ring (64). In the present example, distal arms (80) comprise a unitary plastic material, such that the hinged relationships described above are provided by bending of the material. Alternatively, distal arms (80) may comprise other materials or configurations (e.g., first segment (82) and second segment (84) may be separate pieces joined together).

It will be appreciated that anastomotic ring device (60) may move from an unactuated position to an actuated position (or vice-versa) through hinged flexure of proximal arms (70) and distal arms (80); such that proximal ring (62) moves longitudinally and distally toward middle ring (64), and distal ring (66) moves longitudinally and proximally toward middle ring (64). Anastomotic ring device (60) of the present example is also configured such that it is biased to maintain an actuated position. In other words, an anastomotic ring device (60) that is in an unactuated position may be under a resilient strain to reach an actuated position; and an actuated anastomotic ring device (60) may resist movement toward an unactuated position. Alternatively, anastomotic ring device (60) may have another configuration or other properties, such that anastomotic ring device (60) moves from an unactuated position to an actuated position using some other type of action or structure. By way of example only, anastomotic ring device (60) may be malleable.

In another embodiment (not depicted), arms (70, 80) of anastomotic ring device (60) are substituted with one or more inflatable members. For instance, a proximal inflatable member may be positioned between proximal ring (62) and middle ring (64); and a distal inflatable member between middle ring (64) and distal ring (66). In this embodiment, each of the inflatable members may be in fluid communication with a source of a pressurized medium (e.g., air, liquid, etc.) via applier (10) or via another device. When such inflatable members are not inflated, this alternative anastomotic ring device (60) may be in an unactuated position. When the inflatable members are inflated, the alternative anastomotic ring device (60) may be in an actuated position. In other words, and similar to anastomotic ring device (60) shown in the drawings, this particular alternative anastomotic ring device (60) may have a length that is greater than its width in an unactuated position; and a width that is greater than its length in an actuated position. Alternatively, the effective width of an anastomotic ring device (60), whether it is the anastomotic ring device (60) shown in the drawings, the alternative anastomotic ring device (60) with inflatable members, or in some other embodiment, may otherwise be greater in an actuated position than in an unactuated position (e.g., regardless of whether the length of the device undergoes any change from one position relative another). Still other suitable substitutes and variations of arms (70, 80) will be apparent to those of ordinary skill in the art.

As is also shown in FIGS. 1 and 3-12, proximal arms (70) and distal arms (80) of the present example are radially staggered or offset from one another as to their respective angular positions about the circumference of middle ring (64). Alternatively, proximal arms (70) and distal arms (80) may be positioned along the circumference of middle ring (64) such that they are aligned with each other, or may have any other suitable relative configuration.

In the present example, middle ring (64) comprises a plurality of apertures (68). Apertures (68) are configured to permit passage of an adhesive therethrough, such that apertures (68) act as fluid ports. As will be described in greater detail below, when anastomotic ring device (60) is used to provide and secure an anastomosis, an adhesive may be passed through apertures (68) to provide further sealing and securing of the anastomosis. An exemplary adhesive is disclosed in U.S. Pub. No. 2004/0190975, the disclosure of which is incorporated by reference herein. A suitable adhesive may comprise a cyanoacrylate, an isocyanate, and/or any other suitable substance, including combinations of substances.

Applier (10) of the present example is operable to hold and deploy an anastomotic ring device (60) (e.g., move anastomotic ring device (60) from an unactuated position to an actuated position). Applier (10) is further operable to dispense an adhesive through apertures (68) of middle ring (64) of anastomotic ring device (60). Applier (10) comprises a handle (12) and a shaft (14) extending distally from the handle (12). The distal end of the shaft (14) comprises an introducer tip (16). In the present example, introducer tip (16) is pointed, and is configured to penetrate tissue such as the wall of a stomach (104) and/or a jejunum (102). Alternatively, an introducer tip (16) may be rounded, blunt, or have any other suitable configuration.

As shown in FIGS. 9-14, shaft (14) comprises an actuation portion (20). Actuation portion (20) is operable to hold and actuate an anastomotic ring device (60). Actuation portion (20) comprises a plurality of retaining members (30), a retractable rod (40) within a bore (42), and longitudinal adhesive conduits (50) that are in communication with radial adhesive ports (52). Each of these components will be described in greater detail below.

Retaining members (30) each comprise three radial post members (32) and a resilient member (34). While three radial post members (32) are shown in the present example, it will be appreciated that any other number of radial post members (34) may be used. Radial post members (32) of a given retaining member (30) are engaged with a respective resilient member (34). As shown, resilient member (34) comprises a generally annular ring portion. While resilient member (34) of this example does not form a complete circle, resilient member (34) may form a complete circle (or any other shape or shape portion) in suitable alternative embodiments. Resilient member (34) is biased to have a first diameter, but may be urged to reach and be held at a second diameter that is greater than the first diameter. Accordingly, with radial post members (34) being engaged with a corresponding resilient member (34), a retaining member (30) may be resistingly held such that resilient member (34) is at a second diameter; then the retaining member (30) may radially contract upon release of the retaining member (30), as the bias of resilient member (34) causes resilient member (34) to reach a first diameter.

An example of radial contraction by a retaining member (30) is shown in FIGS. 9-10. In FIG. 9, a distalmost retaining member (30), which is engaged with distal ring (66) of anastomotic ring device (60), is being resistingly held by retractable rod (40), such that resilient member (32) of the distalmost retaining member (30) is at a second diameter. In FIG. 10, retractable rod (40) has released the distalmost retaining member (30), such that the bias of resilient member (32) causes resilient member (32) to reach a first diameter. The movement from the second diameter to the first diameter thus provides a radial contraction. As is also shown in FIGS. 9-10, the distalmost retaining member (30) is operable to selectively maintain the longitudinal position of distal ring (66). In particular, in FIG. 9, with resilient member (32) of distalmost retaining member (30) being at the second diameter, the distalmost retaining member (30) provides an outer diameter that is greater than the inner diameter of the distal ring (66). The distalmost retaining member (30) thereby prevents proximal longitudinal movement of distal ring (66) in the configuration shown in FIG. 9. However, as shown in FIG. 10, with resilient member (32) of distalmost retaining member (30) being at the first diameter, the distalmost retaining member (30) provides an outer diameter that is less than or equal to the inner diameter of the distal ring (66). The distalmost retaining member (30) thereby permits proximal longitudinal movement of distal ring (66) in the configuration shown in FIG. 10. As noted above, where distalmost retaining member (30) permits, anastomotic ring device (30) of the present example is biased such that distal ring (66) will resiliently move in a proximal longitudinal direction toward middle ring (64).

Figure 14:
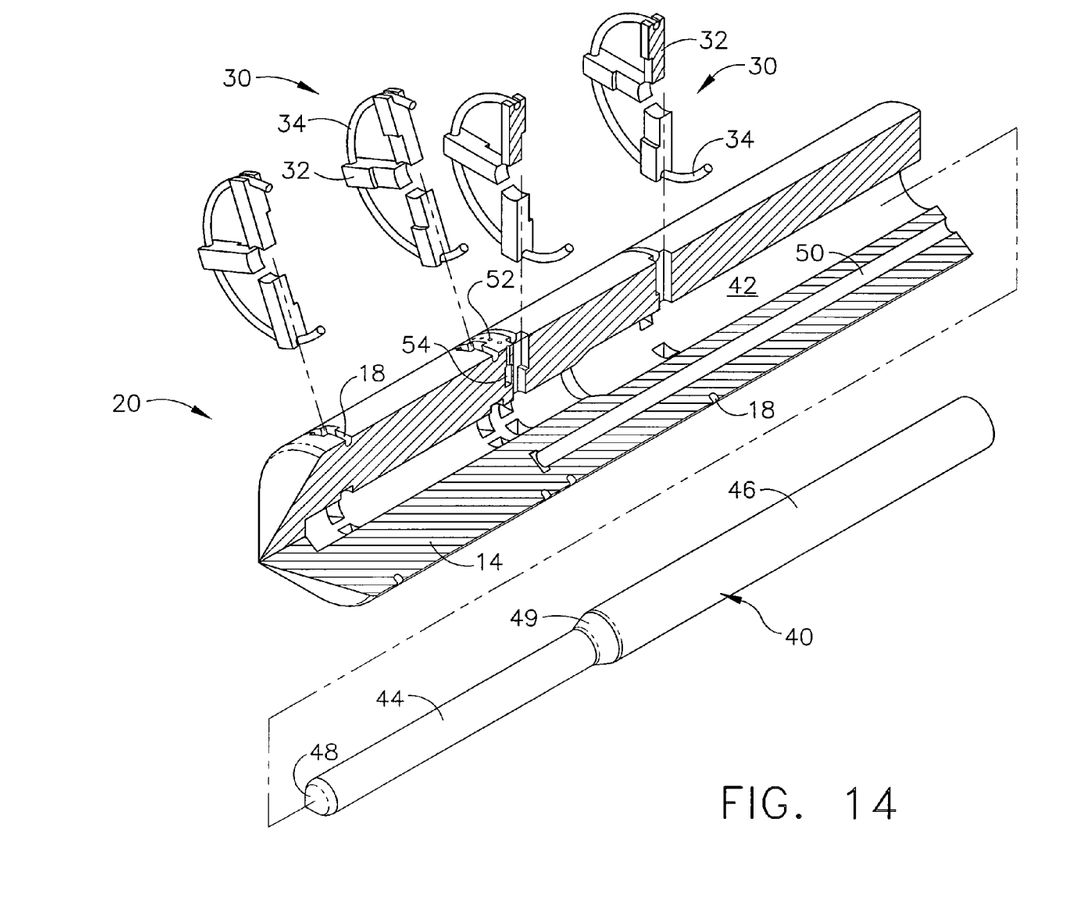
FIG. 14 depicts a perspective exploded partial cross-sectional view of the applier of FIG. 1.

As shown in FIGS. 9-12 and 14, post members (32) and shaft (14) are each configured such that each post member (32) is insertable into shaft (14) in a radial direction. Furthermore, as shown in FIG. 14, shaft (14) has annular recesses (18), each of which is configured to accommodate a corresponding resilient member (34). Other suitable configurations for and relationships between retaining members (30) and shaft (14) will be apparent to those of ordinary skill in the art. Similarly, it will be appreciated that any suitable structures may be used in addition to or in lieu of retaining members (30).

As noted above, shaft (12) further comprises a retractable rod (40) within a bore (42). Retractable rod (40) and bore (42) are aligned along the axis of shaft (12) in the present example, though they may be positioned elsewhere. Retractable rod (40) has a first segment (44) and a second segment (46) that is proximal to the first segment (44). Second segment (46) has a diameter that is greater than the diameter of first segment (44). A tapered tip (48) is provided at the distal end of first segment (44), while a tapered section (49) provides a ramped transition from first segment (44) to second segment (46). In another embodiment, tapered tip (48) is omitted, such that the distal end of first segment (44) is substantially flat. Alternatively, the distal end of first segment may have any other suitable configuration. Similarly, tapered section (49) may have a variety of alternative configurations. By way of example only, tapered section (49) may alternatively be concave, convex, or may be a simple step extending in radial direction. In the present example, bore (42) is configured with surface features mirroring the configuration of the first segment (44), second segment (46), and tapered section (49), though bore (42) may have any other suitable configuration.

As shown in FIG. 9, when retractable rod (40) of the present example is at a distal position, it is configured to push each retaining member (30) outward. In particular, retractable rod (40) engages with post members (32) of each retaining member (30), thereby forcing post members (32) outward under resistance from resilient members (34). In other words, retractable rod (40) is configured to prevent or restrict entry of post members (32) into bore (42). As is also shown in FIG. 9, with retaining members (30) forced outward (e.g., to provide an expanded diameter), retaining members (30) engage rings (62, 64, 66) to hold anastomotic ring device (60) in an unactuated position. In particular, a proximalmost retaining member (30) engages proximal ring (62), thereby preventing proximal ring (62) from moving distally. A distalmost retaining member (30) engages distal ring (66), thereby preventing distal ring (66) from moving proximally. A pair of middle retaining members (30) engage the distal side and proximal side of middle ring (64), thereby preventing any longitudinal movement of middle ring (64).

As shown in FIG. 10, as retractable rod (40) is proximally retracted, tapered tip (48) passes through a transverse plane defined by the distalmost retaining member (30). After such passage, and under resilient urging of resilient member (34), the distalmost retaining member (30) of the present example will radially contract. This radial contraction will provide clearance for distal ring (66) to move proximally, which it will do in the present example at the resilient urging of distal arms (80).

Figure 11:
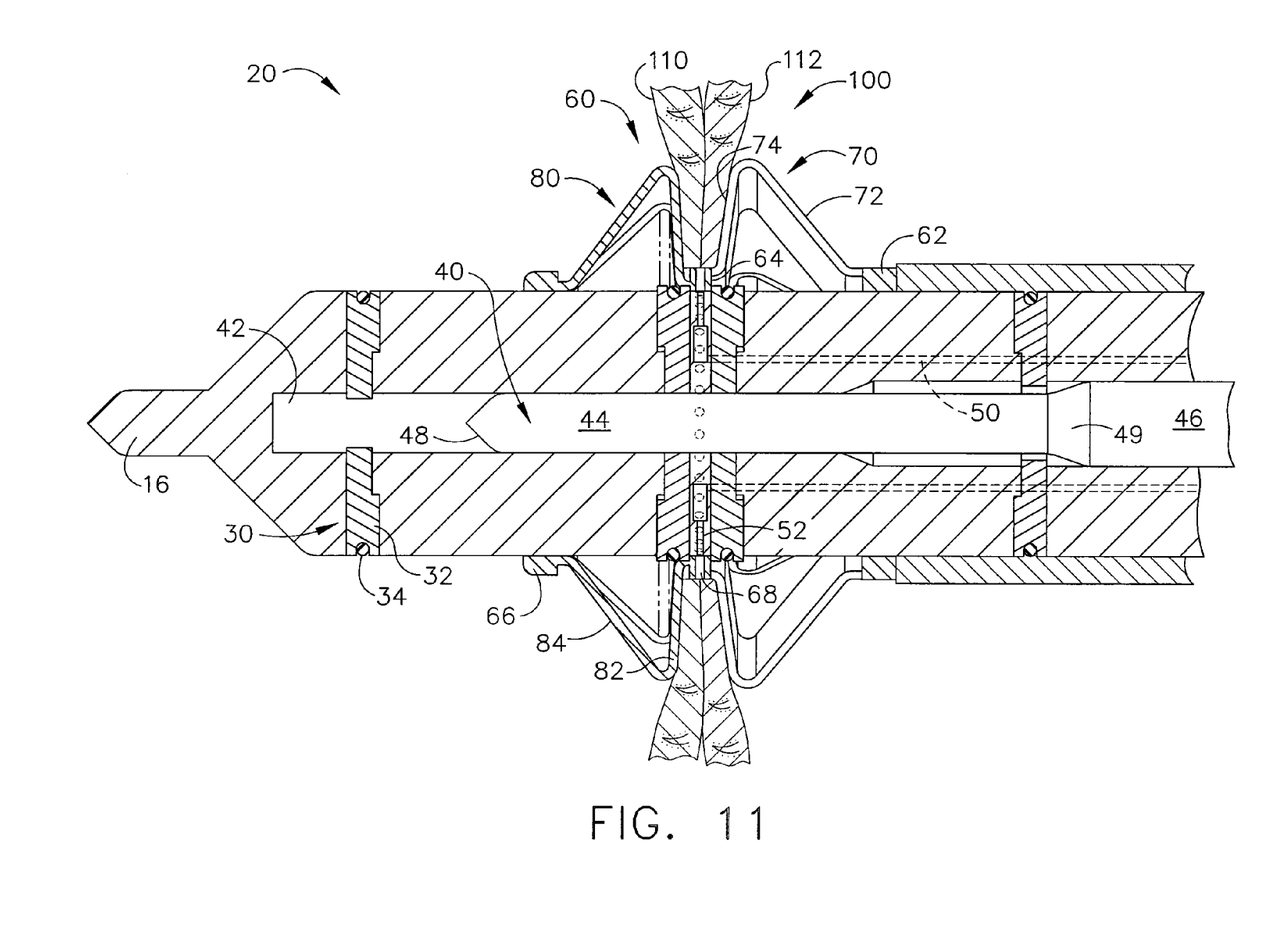
FIG. 11 depicts a partial cross-sectional view of the anastomosis device and applier of FIG. 10, with a proximal portion of the anastomosis device in a deployed configuration.

As shown in FIG. 11, as retractable rod (40) is further proximally retracted, tapered section (49) passes through a transverse plane defined by the proximalmost retaining member (30). After such passage, and under resilient urging of resilient member (34), the proximalmost retaining member (30) of the present example will radially contract. This radial contraction will provide clearance for proximal ring (62) to move distally, which it will do in the present example at the resilient urging of proximal arms (70).

Figure 12:
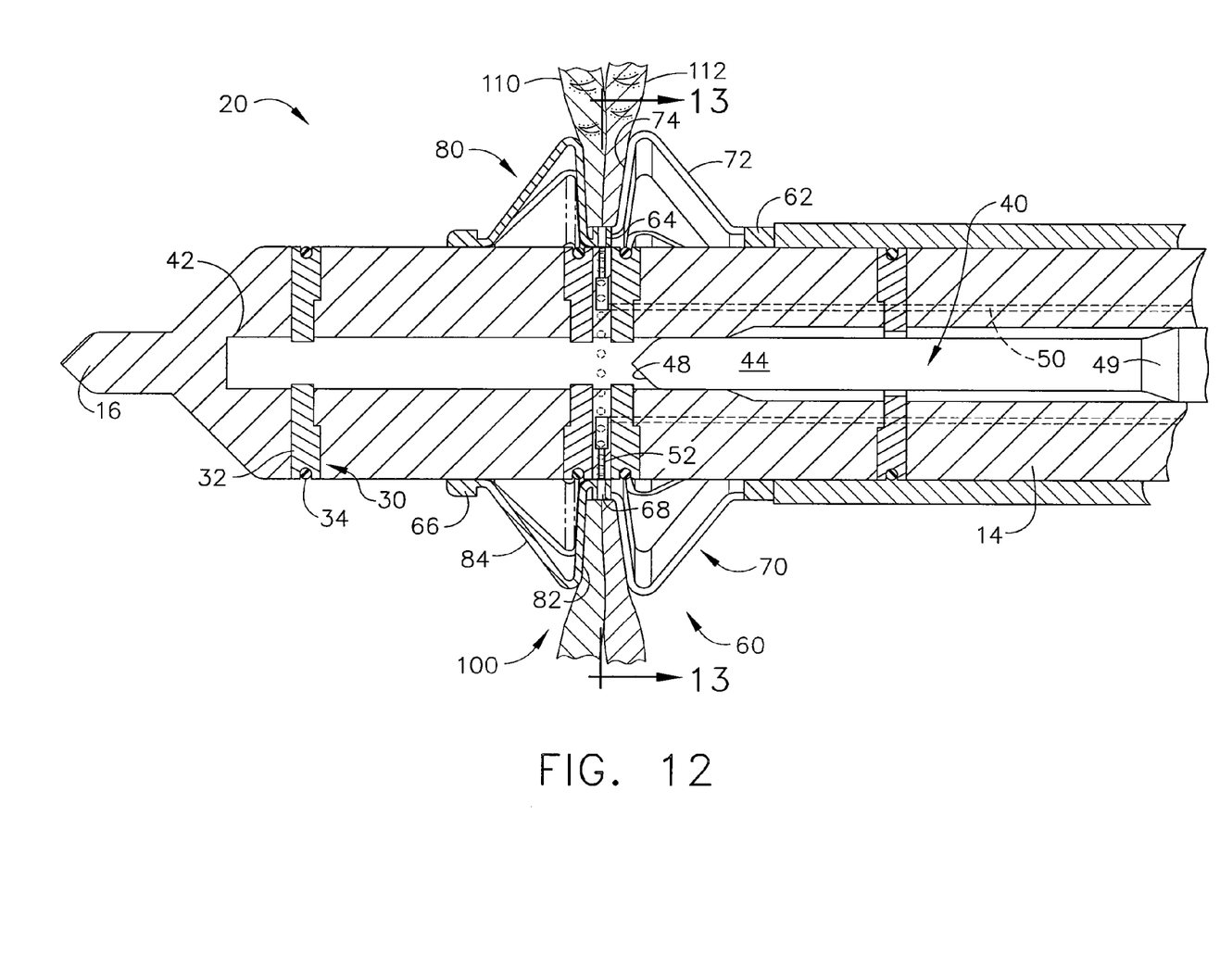
FIG. 12 depicts a partial cross-sectional view of the anastomosis device and applier of FIG. 11, with a retraction rod substantially retracted.
Figure 13:
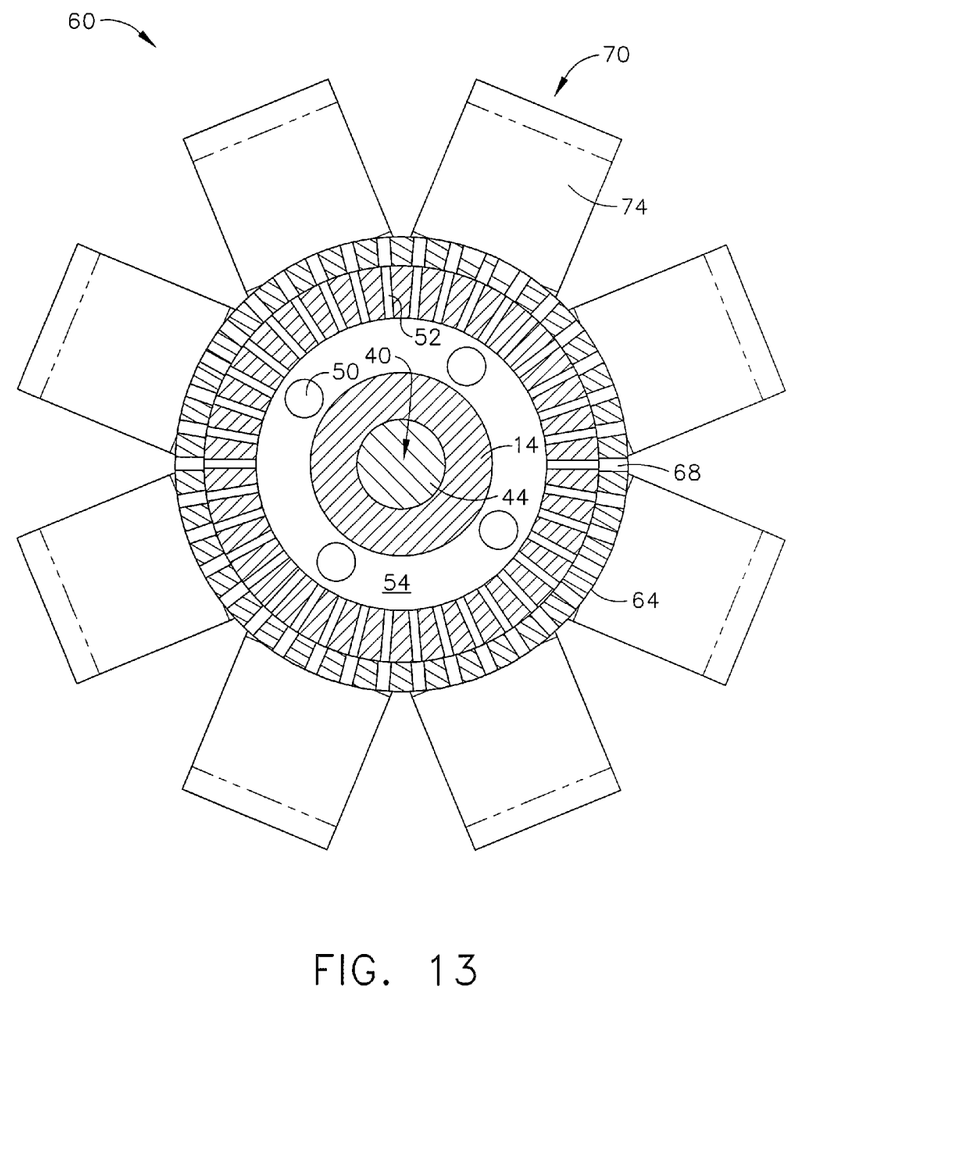
FIG. 13 depicts a cross-sectional view, taken along line 13-13 of FIG. 12.

As shown in FIG. 12, as retractable rod (40) is proximally retracted even further, tapered tip (48) passes through the two transverse planes defined by the two middle retaining members (30). After such passage, and under resilient urging of the resilient members (34) of the two middle retaining members (34), the two middle retaining members (30) will radially contract. This radial contraction will provide clearance for shaft (14) to be moved longitudinally relative to middle ring (64). In particular, where anastomotic ring device (60) has become engaged with tissue by the time the middle retaining members (30) have radially contracted, shaft (14) may be pulled proximally relative anastomotic ring device (60), leaving anastomotic ring device (60) in place engaged with the tissue.

Handle (12) of the present example comprises a grip member (13) and a knob (15). In one embodiment, squeezing the grip member (13) causes retractable rod (40) to retract; while rotation of knob (15) causes adhesive to be dispensed through conduits (50) as described in greater detail below. In another embodiment, squeezing the grip member (13) causes adhesive to be dispensed through conduits (50); while rotation of knob (15) causes retractable rod (40) to retract. Of course, handle (12) may comprise any other suitable features in addition to or in lieu of grip member (13) and knob (15); and any other suitable feature(s) may be used to cause retraction of retractable rod (40) and/or dispensation of adhesive through conduits (50).

As also noted above, and as shown in FIGS. 9-14, shaft (14) of the present example comprises longitudinal adhesive conduits (50) that are in communication with radial adhesive ports (52). Longitudinal adhesive conduits (50) run parallel to the axis of shaft (14), and are in fluid communication with an adhesive source (not shown). By way of example only, an adhesive source may be provided within handle (12) or elsewhere. In the present example, four adhesive conduits (50) are provided. However, it will be appreciated that any other suitable number of adhesive conduits (50) may be provided. The distal end of each adhesive conduit (50) terminates in and is in fluid communication with an annular recess (54), which is longitudinally positioned between the two middle retaining members (30). Radial adhesive ports (52) extend radially outward from and are in fluid communication with annular recess (54). Accordingly, it will be appreciated that an adhesive (or any other fluid) may be communicated through adhesive conduits (50), through annular recess (54), and out of radial adhesive ports (52).

In the present example, the number of radial adhesive ports (52) is equal to the number of apertures (68) in anastomotic ring device (60). Furthermore, radial adhesive ports (52) are configured such that each adhesive port (52) may be radially aligned with a corresponding aperture (68) of anastomotic ring device (60). In the present example, and as shown in FIGS. 7-8, the interior surface of middle ring (64) of anastomotic ring device (60) has a plurality of recesses (86). Each of these recesses (86) is configured to engage with a corresponding protrusion (not shown) on the exterior of shaft (14) in order to facilitate and maintain alignment of ports (52) and apertures (68). In other words, an anastomotic ring device (60) that has been longitudinally positioned on shaft (14) may be rotated about the axis of shaft (14) until the recesses (86) "snap" into place over the protrusions on shaft (14), indicating alignment of ports (52) and apertures (68). Of course, any other feature(s) may be used to facilitate or maintain proper alignment of anastomotic ring device (60) relative to shaft (14). In the present example, however, it will be appreciated that an adhesive (or any other fluid) may be communicated through adhesive conduits (50), through annular recess (54), through radial adhesive ports (52), and out of apertures (68). In particular, an adhesive may be so communicated in order to provide the adhesive at an anastomosis site (100). An adhesive so communicated may provide a seal and/or additional structural integrity to an anastomosis that is provided by and secured by anastomotic ring device (60).

In one embodiment, anastomotic ring device (60) comprises a biodegradable or bioabsorbable plastic material. For instance, anastomotic ring device (60) may degrade at some time after implantation. Anastomotic ring device (60) may be completely or partially absorbed. Alternatively, anastomotic ring device (60) may degrade and fragment, with at least part of the fragments being passed through the patient's gastrointestinal tract. To the extent that an anastomotic ring device (60) has degraded and/or been absorbed, an anastomosis may be maintained by scar tissue, adhesive, and/or by any other device, technique, or phenomenon. Alternatively, an anastomotic ring device (60) may be formed of any other suitable material(s) having any other suitable properties.

In an exemplary use of applier (10) and anastomotic ring device (60), a patient's jejunum (102) is grasped with tissue graspers (106) and positioned adjacent to the patient's stomach (104), such as is shown in FIG. 1. The introducer tip (16) is inserted through the jejunum (102) and stomach (104), as is shown in FIGS. 1 and 9, to position the anastomotic ring device (40) at the anastomosis site (100). During insertion, anastomotic ring device (60) is kept in an unactuated position by retaining members (30). As shown in FIG. 10, the retractable rod (40) is then retracted proximally, which effects actuation of distal arms (80). Shaft (12) is then pulled proximally to cause engagement between first segments (82) of distal arms (80) and inner wall (110) of the patient's stomach (104). As shown in FIG. 11, retractable rod (40) is retracted further proximally, which effects actuation of proximal arms (70). With proximal arms (70) actuated, second segments (74) of proximal arms (70) engage inner wall (112) of the patient's jejunum (102).

Next, in the present exemplary use, adhesive is dispensed at the anastomosis site (100) via apertures (68) as described above. With the adhesive dispensed, and as shown in FIG. 12, retractable rod (40) is retracted proximally even further, such that the middle retaining members (30) release middle ring (64). Applier (10) is then pulled proximally and away from the patient, leaving the deployed, actuated anastomotic ring device (60) at the anastomosis site (100). An exemplary anastomotic ring device (60) left deployed and actuated at an anastomosis site (100) is shown in FIG. 2.

It will be appreciated that any of the foregoing steps in the exemplary use described above may be modified, substituted, supplemented, or omitted as appropriate. Furthermore, it will be appreciated that such a method may be performed using any other suitable devices to substitute, supplement, or modify applier (10) and/or anastomotic ring device (60). By way of example only, applier (10) may be configured such that at least a portion of applier may be passed through a patient's esophagus to reach an anastomosis site (100) from the interior of the stomach (104). Alternatively, applier (10) may be configured such that at least a portion of applier (10) may be presented to an anastomosis site (100) via a trocar or other cannula. In yet another variation, applier (10) is configured to be used in an open procedure. Still other structural and procedural variations will be apparent to those of ordinary skill in the art.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. the sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An anastomosis device operable to provide an anastomosis between two tissue walls, the anastomosis device comprising:
    an anastomotic ring device, the anastomotic ring device comprising:
        (a) a proximal ring defining a first opening,
        (b) a distal ring defining a second opening, wherein the second opening is substantially coaxially aligned with the first opening,
        (c) a center member positioned longitudinally between the proximal ring and the distal ring, wherein the center member comprises at least one transverse fluid port, wherein the fluid port is configured to communicate a fluid medium, wherein the center member defines a third opening, wherein the third opening is substantially coaxially aligned with the first and second openings,
        (d) a proximal expandable portion joining the proximal ring to the center member, and
        (e) a distal expandable portion joining the distal ring to the center member;
    wherein the anastomotic ring device is configured to move from an unactuated position to an actuated position, wherein a first portion the anastomotic ring device has a first width when the anastomotic ring device is in the unactuated position, wherein the first portion of the anastomotic ring device has a second width when the anastomotic ring device is in the actuated position, wherein the second width is greater than the first width, wherein a second portion of the anastomotic ring device has a third width when the anastomotic ring device is in the unactuated position and when the anastomotic ring device is in the actuated position, wherein the second width is greater than the third width, wherein the first, second, and third openings together define an open passageway when the anastomotic ring device is in the actuated position, wherein the open passageway is configured to permit fluid communication through the proximal and distal rings, through the center member, and through the two tissue walls, wherein the transverse fluid port is transverse to the open passageway; and
    an applier, wherein the anastomotic ring device is engaged with the applier, wherein the applier has at least one radial adhesive port, wherein the at least one radial adhesive port of the applier is radially aligned with the at least one transverse fluid port of the center member of the anastomotic ring device.

2. The anastomosis device of claim 1, wherein the distal expandable portion comprises a plurality of segmented arms.

3. The anastomosis device of claim 2, wherein each of the segmented arms comprises a pair of segments, wherein each segment of a pair is hingedly joined with the other segment of the corresponding pair.

4. The anastomosis device of claim 2, wherein the each of the segmented arms is hingedly connected with one or both of the distal ring or the center member.

5. The anastomosis device of claim 1, wherein the third width is substantially equal to the first width when the anastomosis device is in the unactuated position.

6. The anastomosis device of claim 1, wherein the center member comprises a center ring.

7. The anastomosis device of claim 6, wherein the at least one transverse fluid port comprises at least one aperture extending radially through the center ring.

8. The anastomosis device of claim 1, wherein the anastomotic ring device is resiliently biased toward the actuated position.

9. The anastomosis device of claim 1, wherein the anastomotic ring device is formed from a biodegradable material.

10. The anastomosis device of claim 1, wherein the at least one transverse fluid port is in fluid communication with an adhesive source.

11. The anastomosis device of claim 1, wherein the applier further comprises a conduit in fluid communication with the at least one radial adhesive port of the applier.

12. The anastomosis device of claim 1, wherein the anastomotic ring device is resiliently biased toward the actuated position, wherein the applier is operable to hold the anastomotic ring device in the unactuated position in resistance to the resilient bias toward the actuated position.

13. The anastomosis device of claim 1, wherein the applier further comprises a shaft, wherein the anastomotic ring device is engaged with the shaft of the applier, wherein the applier is operable to deploy the anastomotic ring device at an anastomosis site.

14. The anastomosis device of claim 13, wherein the applier further comprises a plurality of retaining members, wherein the retaining members are configured to selectively maintain the longitudinal position of each of the distal ring, proximal ring, and center member relative to the shaft of the applier.

15. The anastomosis device of claim 14, wherein the retaining members are generally annular, wherein the retaining members are configured to radially expand or contract.

16. The anastomosis device of claim 15, wherein the applier further comprises a retractable member, wherein the retractable member is operable to selectively engage the retaining members in order to selectively effect radial expansion or contraction of the retaining members.

17. A method of using the anastomosis device of claim 13 to anastomose tissue at an anastomosis site, the method comprising:
    positioning the anastomotic ring device at an anastomosis site;
    deploying the anastomotic ring device at the anastomosis site, using the applier, to create an anastomosis; and
    applying an adhesive at the anastomosis site, wherein the adhesive is applied adjacent to the anastomotic ring device.

18. The method of claim 17, wherein the act of applying the adhesive comprises communicating the adhesive radially outwardly through the at least one transverse fluid port of the anastomotic ring device.

19. The method of claim 18, wherein the shaft of the applier comprises at least one conduit in fluid communication with the at least one transverse fluid port of the anastomotic ring device, wherein the act of applying the adhesive further comprises communicating the adhesive through the at least one conduit of the applier.

* * * * *